(12) United States Patent
Chen et al.

(10) Patent No.: US 12,226,306 B2
(45) Date of Patent: Feb. 18, 2025

(54) AORTIC STENT-GRAFT

(71) Applicant: Hongwei Chen, Quanzhou (CN)

(72) Inventors: Hongwei Chen, Quanzhou (CN); Weiguo Fu, Shanghai (CN); Lixin Wang, Shanghai (CN)

(73) Assignee: Hongwei Chen, Quanzhou (CN)

( * ) Notice: Subject to any disclaimer, the term of this patent is extended or adjusted under 35 U.S.C. 154(b) by 756 days.

(21) Appl. No.: 17/426,654

(22) PCT Filed: Jan. 17, 2020

(86) PCT No.: PCT/CN2020/072625
§ 371 (c)(1),
(2) Date: Jul. 29, 2021

(87) PCT Pub. No.: WO2020/156219
PCT Pub. Date: Aug. 6, 2020

(65) Prior Publication Data
US 2022/0047376 A1     Feb. 17, 2022

(30) Foreign Application Priority Data

Jan. 31, 2019   (CN) .................. 201920168771.X

(51) Int. Cl.
*A61F 2/07*    (2013.01)
*A61F 2/06*    (2013.01)

(52) U.S. Cl.
CPC .......... *A61F 2/07* (2013.01); *A61F 2002/061* (2013.01); *A61F 2002/072* (2013.01); *A61F 2002/075* (2013.01); *A61F 2220/0075* (2013.01)

(58) Field of Classification Search
CPC .......... A61F 2002/061; A61F 2002/072; A61F 2002/075; A61F 2220/0075
See application file for complete search history.

(56) References Cited

U.S. PATENT DOCUMENTS 11,559,386 B2 *   1/2023   Ehnes ................. A61F 2/88
2011/0257731 A1   10/2011  Hartley et al.
(Continued)

FOREIGN PATENT DOCUMENTS

| CN | 102973303 A | 3/2013 |
| CN | 102973303 B | 2/2015 |

(Continued)

*Primary Examiner* — Jerrah Edwards
*Assistant Examiner* — Aren Patel
(74) *Attorney, Agent, or Firm* — Bayramoglu Law Offices LLC

(57) ABSTRACT

An aortic stent-graft includes a main aortic stent-graft and a plurality of branch arterial stent-grafts. The main aortic stent-graft includes a proximal segment, a depressed segment, and a distal segment; steps are provided on a top surface of the depressed segment from left to right; one or two first orifices are formed on a middle-upper part of a right side wall of the proximal segment, and one or two second orifices are formed on a right side wall of the steps; a first inner chimney stent is fixed inside the first orifice and a second inner chimney stent is fixed inside the second orifice; the first inner chimney stent is sutured along an inner wall of the proximal segment, and the second inner chimney stent is sutured along an inner wall of the steps; and one of the branch arterial stent-grafts is placed inside each inner chimney stent.

7 Claims, 8 Drawing Sheets

(56) References Cited

U.S. PATENT DOCUMENTS

| | | | | |
|---|---|---|---|---|
| 2017/0325977 A1* | 11/2017 | Sarac | .......... | A61F 2/07 |
| 2018/0153688 A1* | 6/2018 | O'Connor | .......... | A61F 2/2436 |
| 2019/0083229 A1* | 3/2019 | Szente Varga | .......... | A61F 2/07 |
| 2020/0000592 A1* | 1/2020 | Lee | .......... | A61F 2/2418 |
| 2020/0170778 A1* | 6/2020 | Ehnes | .......... | A61F 2/88 |
| 2020/0352699 A1* | 11/2020 | Guo | .......... | A61F 2/07 |

FOREIGN PATENT DOCUMENTS

| | | |
|---|---|---|
| CN | 206534738 U | 10/2017 |
| CN | 109009562 A | 12/2018 |
| CN | 109009563 A | 12/2018 |
| CN | 209808643 U | 12/2019 |

\* cited by examiner

AORTIC STENT-GRAFT

CROSS REFERENCE TO THE RELATED APPLICATIONS

This application is the national phase entry of International Application No. PCT/CN2020/072625, filed on Jan. 17, 2020, which is based upon and claims priority to Chinese Patent Application No. 201920168771.X, filed on Jan. 31, 2019, the entire contents of which are incorporated herein by reference.

TECHNICAL FIELD

The present invention relates to the field of implantable stent-grafts, and more specifically to an aortic stent-graft.

BACKGROUND

The applicant of the present invention previously proposed an aortic arch covered stent-graft, as disclosed in Chinese patent No. 102973303B. The aortic arch covered stent-graft includes an aortic stent-graft and three branch arterial stent-grafts, where a depressed segment is provided on the aortic stent-graft. The depressed segment includes a left side wall close to a proximal end, a right side wall far from the proximal end, and a bottom wall connecting the left side wall and the right side wall. Two orifices are formed on the left side wall of the depressed segment. One or two orifices are formed on the right side wall. An inner chimney stent is fixed inside each orifice, and the inner chimney stent has a caliber adapted to the caliber of the orifice. The inner chimney stent extends along the side wall of the aortic stent-graft that is away from the depressed segment. The branch arterial stent-grafts are placed inside the inner chimney stents, respectively. In the stent-graft with this structure, three or four orifices are formed on the left and right side walls of the depressed segment, and communicate with the inner chimney stents. The branch arterial stent-grafts are implanted into three main branch arterial blood flow channels through the optimal route selected from the several inner chimney stents without the need of customization according to the specific anatomy of a patient. The aortic stent-graft and the branch arterial stent-grafts of this patent are independent structures, which are suitable for various normal and abnormal blood vessels. The aortic stent-graft and branch arterial stent-grafts of suitable sizes can be selected according to the specific conditions of a lesion to assemble a stent-graft system that is most suitable for the patient.

When the above-mentioned stent-graft is implanted in an aortic lesion, at least one of the branch arterial stent-grafts must be constructed from any one of brachiocephalic trunk (BCT), left common carotid artery (LCCA), and left subclavian artery (LSA) to the inner chimney stent at the right side of the depressed segment. However, when a branch arterial stent-graft is constructed from the right side of the depressed segment to the LSA, the branch arterial stent-graft has a large angular distortion, thus producing a large resilience force, which causes greater pressure to a blood vessel at the corresponding position, and even leads to the rupture of the blood vessel. Moreover, the angular distortion of the branch arterial stent-graft causes stenosis in the stent, thereby affecting the patency of blood flow in the stent. In view of the above, the inventor proposes some improvements.

SUMMARY

The present invention provides an aortic stent-graft to solve the problem that the existing aortic covered stent-graft has large angular distortion and produces a large resilience force, which causes greater pressure to a blood vessel at the corresponding position, and also will cause stenosis in the stent and affect the patency of blood flow in the stent.

The present invention adopts the following technical solutions:

An aortic stent-graft is provided, including a main aortic stent-graft and a plurality of branch arterial stent-grafts, where the main aortic stent-graft includes a proximal segment, a distal segment, and a depressed segment that connects the proximal segment and the distal segment; at least one step is provided on a top surface of the depressed segment from left to right; one or two first orifices are formed on a middle-upper part of a right side wall of the proximal segment, and one or two second orifices are formed on a right side wall of the step; a first inner chimney stent is fixed inside the first orifice and a second inner chimney stent is fixed inside the second orifice; the first inner chimney stent is sutured along an inner wall of the proximal segment, and the second inner chimney stent is sutured along an inner wall of the step; and one of the branch arterial stent-grafts is placed inside each of the first inner chimney stent and the second inner chimney stent.

Preferably, the main aortic stent-graft may be in a straight cylindrical shape or a pre-curved shape.

Further, no orifice may be formed on a left side wall of the distal segment.

Further, a left segment of the distal segment that is connected to the depressed segment may be formed by connecting a cylindrical part and a conical part, where a front end of the conical part that is connected to the cylindrical part may have a caliber smaller than a caliber of a rear end of the conical part.

Further, the left segment of the distal segment that is connected to the depressed segment may gradually expand from left to right.

In a preferred embodiment, the top surface of the depressed segment may be provided with one step, and a left side of the step may be connected to a middle-lower part of the right side wall of the proximal segment through a covering membrane.

Specifically, two first orifices may be formed on the middle-upper part of the right side wall of the proximal segment, and one first inner chimney stent may be fixed in each of the first orifices; and one second orifice may be formed on the right side wall of the step.

Further, a right end surface of the step may be an inclined surface, and the inclined surface may form an obtuse angle with an axis of the main aortic stent-graft; and the second orifice may be an oblique incision formed on the inclined surface.

In another preferred embodiment, the depressed segment may be provided with a first step and a second step sequentially from left to right; a left side of the first step may be fixedly connected to the middle-lower part of the right side wall of the proximal segment through a first covering membrane; and a left side of the second step may be fixedly connected to a middle-lower part of a right side wall of the first step.

Further, one first orifice may be formed on an upper part of the right side wall of the proximal segment, and one first inner chimney stent may be fixed inside the first orifice; and one second orifice may be formed on an upper part of each of the right side wall of the first step and a right side wall of the second step, and one second inner chimney stent may be fixed inside the second orifice.

Further, one first orifice may be formed on the upper part of the right side wall of the proximal segment, and one first inner chimney stent may be fixed inside the first orifice; and one second orifice may be formed on the upper part of the right side wall of the first step, two second orifices may be formed on the right side wall of the second step, and one second inner chimney stent may be fixed inside each of the second orifices.

Further, the aortic stent-graft may further include a plurality of built-in guide wires, and one of the built-in guide wires can be placed inside the first inner chimney stent and/or the second inner chimney stent.

It can be seen from the above description of the structure of the present invention that, compared with the prior art, the present invention has the following advantages:

1. In the aortic stent-graft of the present invention, steps are provided from left to right on the depressed segment of the main aortic stent-graft, and inner chimney stents are fixed in the proximal segment and the steps, respectively. Therefore, when branch arterial stent-grafts are constructed from the inner chimney stents in the proximal segment and steps to the three branch stent-grafts of human body, there is a large operating space and the constructed branch arterial stent-grafts have small angular distortion, which is convenient for the delivery and release of the branch arterial stent-grafts; and the blood flow after the construction is more in line with the anatomy and physiology, that is, the internal space of the stent is not affected and the blood flow is smooth.

2. A right end surface of the first step of the present invention is an inclined surface, the second orifice fixed with the second inner chimney stent is provided as an oblique incision correspondingly, and the inclined surface forms an obtuse angle with a bottom wall of the depressed segment to facilitate the delivery of the branch arterial stent-grafts.

3. The aortic stent-graft of the present invention, when having four orifices, can be used for the construction of an abdominal aorta in the case where a lesion is on a renal artery.

4. In the aortic stent-graft of the present invention, built-in guide wires are placed inside the first inner chimney stent and/or the second inner chimney stent to quickly and accurately place the branch arterial stent-grafts into the first inner chimney stent and/or the second inner chimney stent, thereby shortening the operation time.

DETAILED DESCRIPTION OF THE EMBODIMENTS

Figure 1:
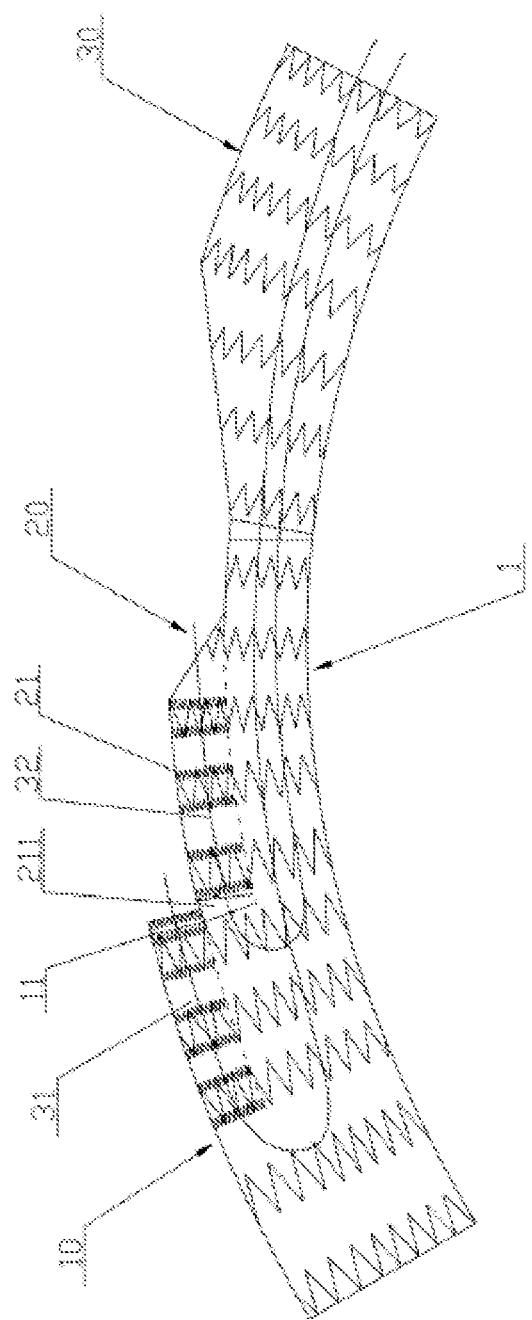
FIG. 1 is a front view of the main aortic stent-graft according to Example 1 of the present invention.
Figure 2:
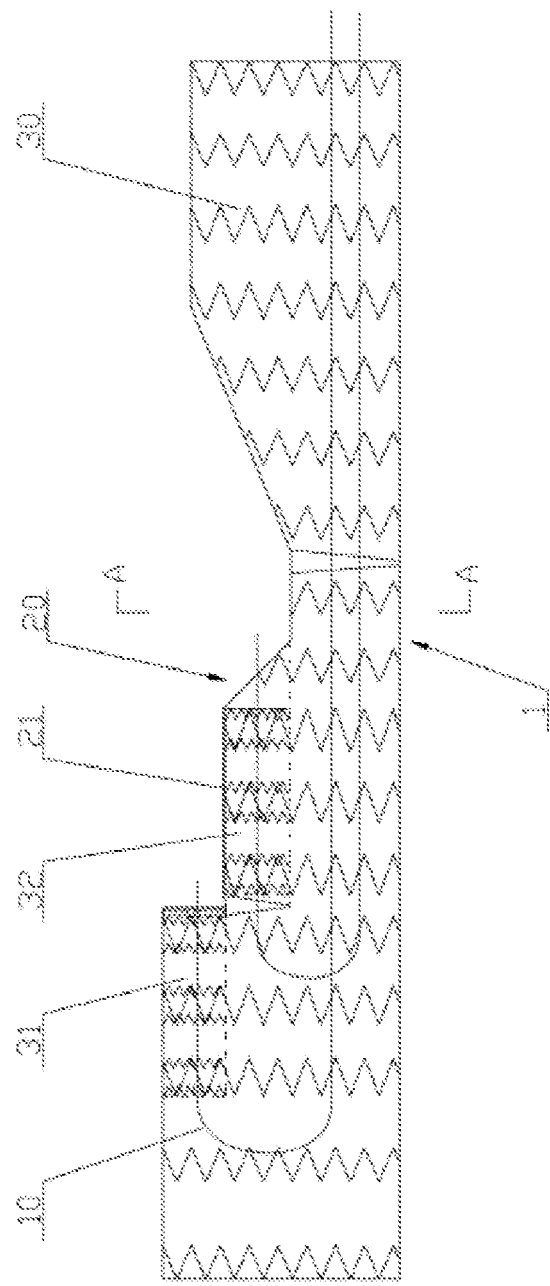
FIG. 2 is a schematic diagram of the main aortic stent-graft according to Example 1 of the present invention that is stretched into a straight state.
Figure 3:
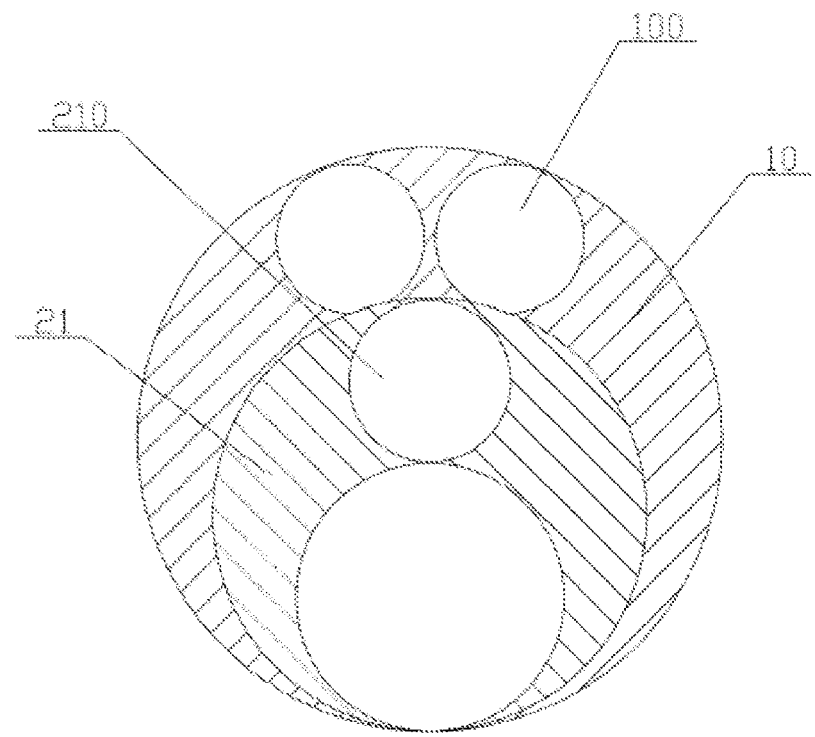
FIG. 3 is a cross-sectional view obtained in an A-A direction of FIG. 2.
Figure 4:
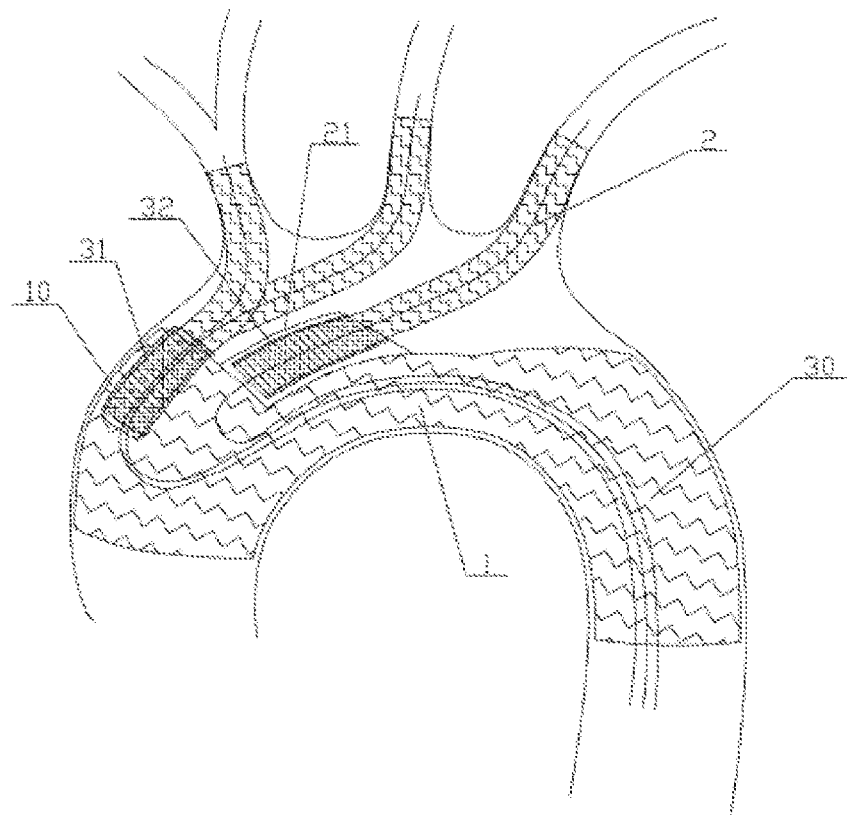
FIG. 4 is a schematic structural diagram of the stent-graft according to Example 1 of the present invention, where the stent-graft is released in a thoracic aorta and three branch arterial stent-grafts are placed for branch arterial stent-grafts.
Figure 5:
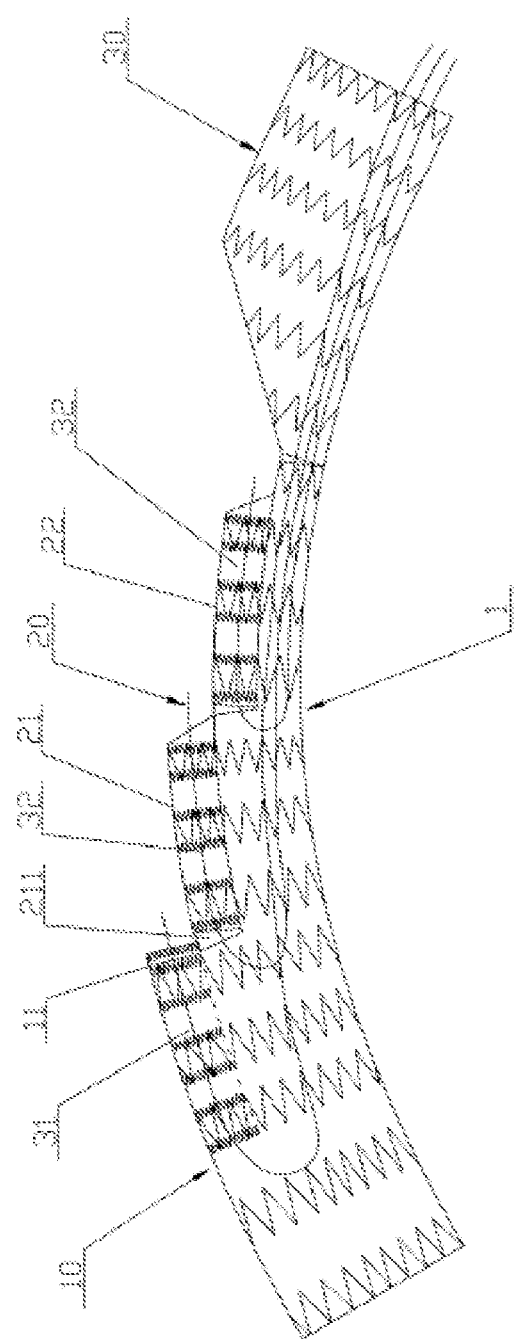
FIG. 5 is a front view of the aortic stent-graft according to Example 2 of the present invention.

Specific implementations of the present invention will be described below with reference to the accompanying drawings.

In the various examples of the present invention, well-known structures or materials are not shown or not described in detail. Moreover, the described features, structures, or characteristics can be combined in any manner in one or more implementations. In addition, those skilled in the art should understand that the various implementations below are only used for illustration, and are not intended to limit the protection scope of the present invention. It can also be easily understood that the components in the various implementations described herein and shown in the drawings can be arranged and designed in a variety of different configurations or scales.

EXAMPLE 1

An aortic stent-graft includes a main aortic stent-graft 1 and three branch arterial stent-grafts 2. The main aortic stent-graft 1 has a pre-curved shape, and a pre-curving degree of the main aortic stent-graft 1 is less than or equal to a curving degree of a human aortic arch. The main aortic stent-graft 1 includes a proximal segment 10, a distal segment 30, and a depressed segment 20 that connects the proximal segment 10 and the distal segment 30.

One step 21 is provided on a top surface of the depressed segment 20, and a left side of the step 21 is fixedly connected to a middle-lower part of a right side wall of the proximal segment 10 through a covering membrane 211; two first orifices 100 are formed on a middle-upper part of a right side wall of the proximal segment 10, and one second orifice 210 is formed on a right side wall of the step 21; a first inner chimney stent 31 is fixed inside the first orifice 100 and a second inner chimney stent 32 is fixed inside the second orifice 210; the first inner chimney stent 31 is sutured along an inner wall of the proximal segment 10, and the second inner chimney stent 32 is sutured along an inner wall of the step 21; and one of the branch arterial stent-grafts 2 is placed inside each of the first inner chimney stent 31 and the second inner chimney stent 32.

No orifice is formed on a left segment of the distal segment 30 that is connected to the depressed segment 20, and the left segment may be formed by connecting a cylindrical part and a conical part, where a front end of the conical part that is connected to the cylindrical part may have a caliber smaller than a caliber of a rear end of the conical part. The left segment of the distal segment that is connected to the depressed segment may also gradually expand from left to right.

In order to facilitate the delivery of the branch arterial stent-grafts 2, a right end of the first inner chimney stent 31 protrudes from the first orifice 100 by a length of 3 mm to 5 mm.

A right end surface of the step 21 is an inclined surface, and the inclined surface forms an obtuse angle with an axis of the main aortic stent-graft; and the second orifice 210 is an oblique incision formed on the inclined surface to facilitate the delivery of the branch arterial stent-grafts 2 into the second inner chimney stent 32.

The built-in guide wire 3 is placed inside the first inner chimney stent 31 and/or the second inner chimney stent 32 to place the branch arterial stent-grafts 2 into the first inner chimney stent 31 and/or the second inner chimney stent 32.

A top end, a bottom end, a front end, and a rear end of an outer circumference of the first inner chimney stent fixed in the first orifice 100 each are provided with an 8-shaped developing mark 11, and a top end, a bottom end, a front end, and a rear end of an outer circumference of a front head of the first inner chimney stent 31 that protrudes from the first orifice 100 each are also provided with an 8-shaped developing mark 11. A top end, a bottom end, a front end, and a rear end of an outer circumference of the second inner chimney stent 32 fixed in the second orifice 210 each are provided with an 8-shaped developing mark 11. The above-mentioned 8-shaped developing marks 11 are all arranged obliquely along an axial direction of the main aortic stent-graft 1. The 8-shaped developing marks 11 are an inherent ingredient of the stent itself, or a material with prominent biocompatibility and X-ray opacity.

EXAMPLE 2

As shown in FIG. 5 to FIG. 8, an aortic stent-graft in this example also includes a main aortic stent-graft 1 and three branch arterial stent-grafts 2. The main aortic stent-graft 1 also includes a proximal segment 10, a distal segment 30, and a depressed segment 20 that connects the proximal segment 10 and the distal segment 30. This example is different from Example 1 mainly in that the depressed segment 20 is provided with a first step 21 and a second step 22 from left to right; a left side of the first step 21 is fixedly connected to a middle-lower part of a right side wall of the proximal segment 10 through a first covering membrane 211; and a left side of the second step 22 is fixedly connected to a middle-lower part of a right side wall of the first step 21 through a second covering membrane 221.

Figure 6:
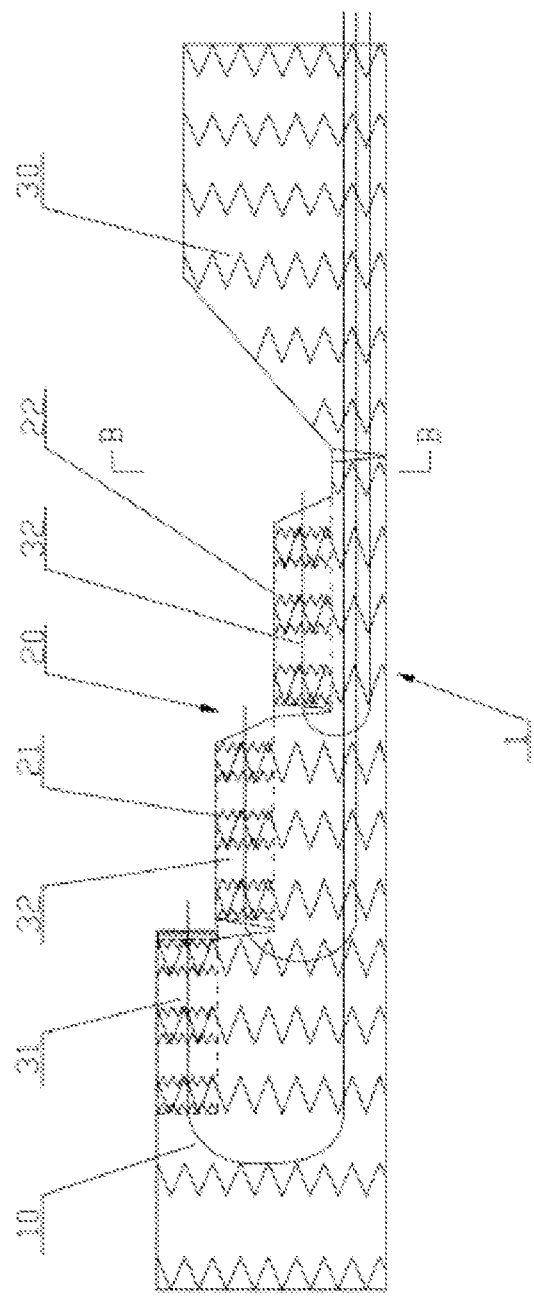
FIG. 6 is a schematic diagram of the aortic stent-graft according to Example 2 of the present invention that is stretched into a straight state.
Figure 7:
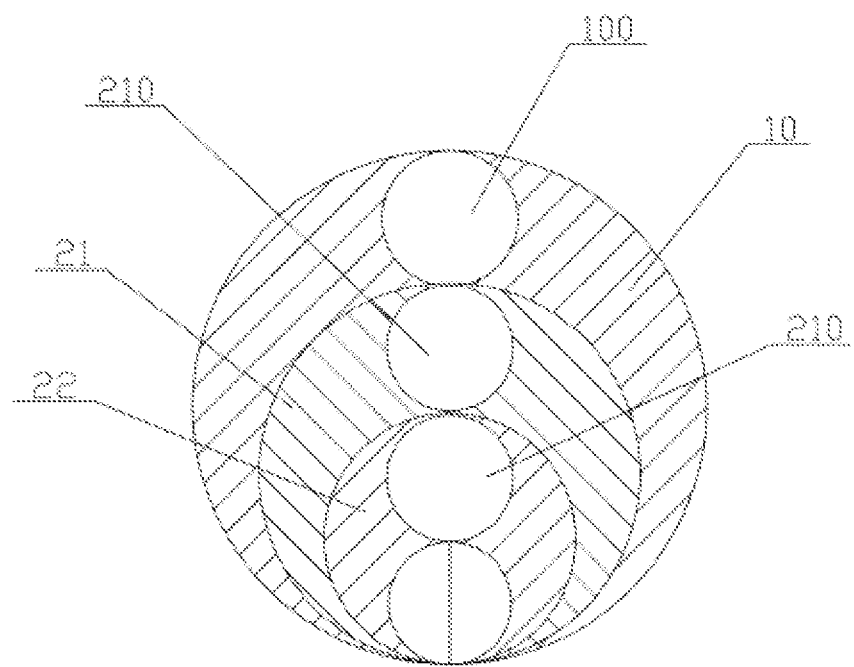
FIG. 7 is a cross-sectional view obtained in a B-B direction of FIG. 6.
Figure 8:
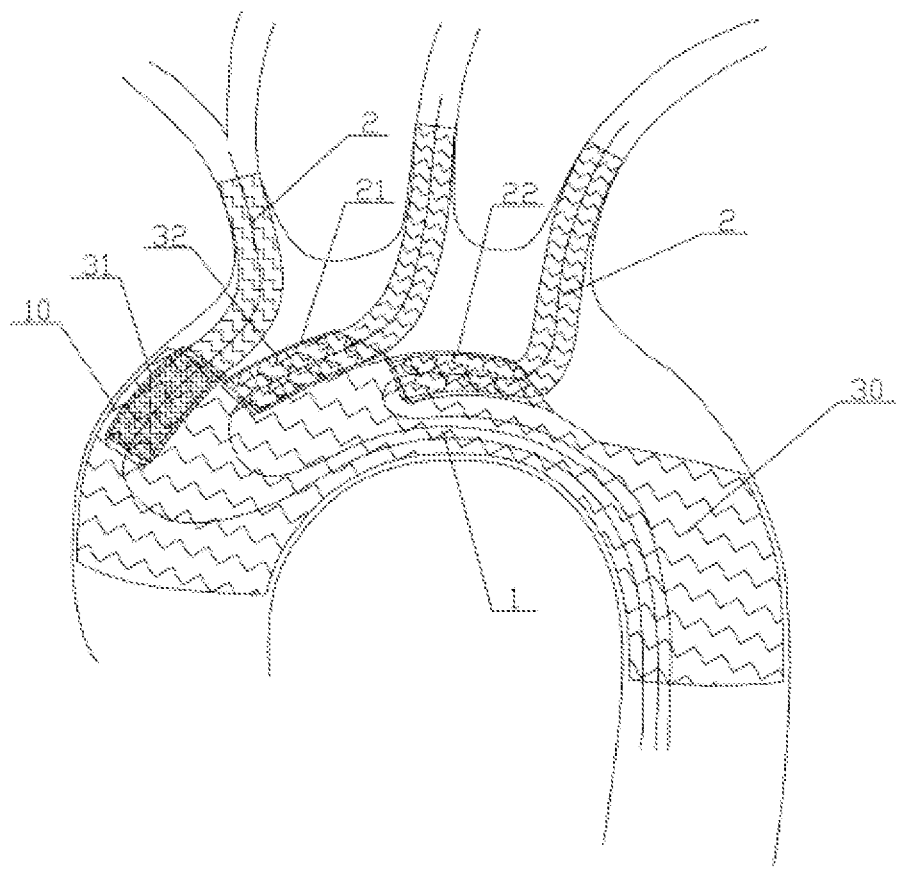
FIG. 8 is a schematic structural diagram of the stent-graft according to Example 2 of the present invention, where the stent-graft is released in a thoracic aorta and three branch arterial stent-grafts are placed for branch arterial stent-grafts.

As shown in FIG. 6 and FIG. 7, in this example, one first orifice 100 is formed on an upper part of the right side wall of the proximal segment 10, and a first inner chimney stent 31 is fixed in the first orifice 100; one second orifice 210 is formed on an upper part of each of the right side wall of the first step 21 and a right side wall of the second step 22, and one second inner chimney stent 32 is fixed inside the second orifice 210; and one of the branch arterial stent-grafts 2 is placed inside each of the first inner chimney stent 31 and the second inner chimney stents 32.

As shown in FIG. 6, in this example, no orifice is formed on a left segment of the distal segment 30 that is connected to the depressed segment 20, and the left segment may be formed by connecting a cylindrical part and a conical part, where a front end of the conical part that is connected to the cylindrical part may have a caliber smaller than a caliber of a rear end of the conical part. The left segment of the distal segment 30 that is connected to the depressed segment 20 may also gradually expand from left to right.

The built-in guide wire 3 is placed inside the first inner chimney stent 31 and/or the second inner chimney stent 32 to place the branch arterial stent-grafts 2 into the first inner chimney stent 31 and/or the second inner chimney stent 32.

EXAMPLE 3

Figure 9:
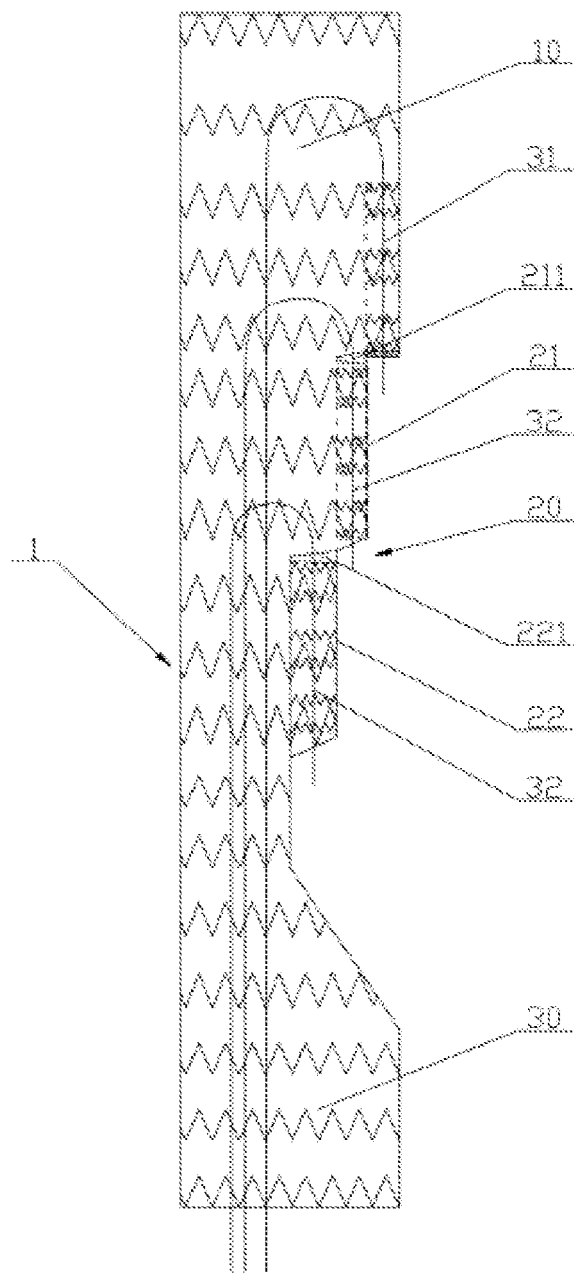
FIG. 9 is a front view of the aortic stent-graft according to Example 3 of the present invention.
Figure 10:
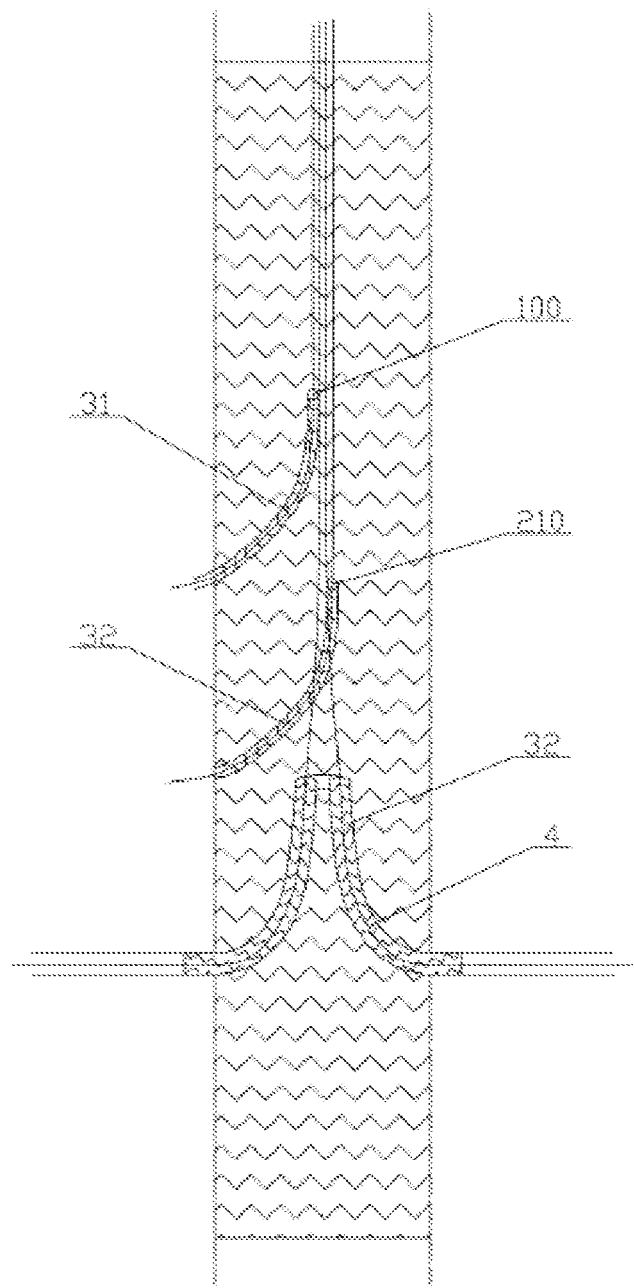
FIG. 10 is a schematic structural diagram of the stent-graft according to Example 3 of the present invention, where the stent-graft is released in an abdominal aorta and four branch arterial stent-grafts are placed for branch arterial stent-grafts.

As shown in FIG. 9 and FIG. 10, an aortic stent-graft in this example includes a main aortic stent-graft 1 and four branch arterial stent-grafts 2 and can be used for the construction of an abdominal aorta in the case where a lesion is on a renal artery. The main aortic stent-graft 1 also includes a proximal segment 10, a distal segment 30, and a depressed segment 20 that connects the proximal segment 10 and the distal segment 30. The depressed segment 20 is provided with a first step 21 and a second step 22 from left to right; a left side of the first step 21 is fixedly connected to a middle-lower part of a right side wall of the proximal segment 10 through a first covering membrane 211; and a left side of the second step 22 is fixedly connected to a middle-lower part of a right side wall of the first step 21 through a second covering membrane 221.

This example is different from Example 2 mainly in that one first orifice 100 is formed on an upper part of the right side wall of the proximal segment 10, and a first inner chimney stent 31 is fixed in the first orifice 100; one second orifice 210 is formed on an upper part of the right side wall of the first step 21, two second orifices 210 are formed on a right side wall of the second step 22, and one second inner chimney stent 32 is fixed in each of the second orifices 210; and one of the branch arterial stent-grafts 2 is placed inside each of the first inner chimney stent 31 and the second inner chimney stents 32.

The aortic stent-graft in this example further includes four guide wires 4, which pass through the first orifice 100 and the second orifices 210 respectively, and extend into the corresponding first inner chimney stent 31 or second inner chimney stent 32.

Because the celiac trunk artery, superior mesenteric artery (SMA), left renal artery, and right renal artery on the abdominal aorta have small diameters and the outer diameters of the first and second inner chimney stents must match with the diameters, the outer diameters of the first and second inner chimney stents in this example are smaller than the outer diameters of the first and second inner chimney stents in Examples 1 and 2.

The above are merely specific implementations of the present invention, but the design concept of the present invention is not limited thereto. Any non-substantial changes made to the present invention based on the concept should fall inside the protection scope of the present invention.

What is claimed is:

1. An aortic stent-graft, comprising
a main aortic stent-graft and a plurality of branch arterial stent-grafts, wherein the main aortic stent-graft comprises
a proximal segment,
a distal segment, and
a depressed segment connecting the proximal segment and the distal segment;
a first step and a second step sequentially from left to right are provided on a top surface of the depressed segment, wherein a left side of the first step is fixedly connected to a middle-lower part of the right side wall of the proximal segment through a first covering membrane; and a left side of the second step is fixedly connected to a middle-lower part of a right side wall of the first step through a second covering membrane;

a first orifice is formed on a middle-upper part of a right side wall of the proximal segment, one or two second orifices are formed on a right side wall of the first step, and one or two second orifices are formed on a right side wall of the second step;

a first inner chimney stent is fixed inside the first orifice and one or two second inner chimney stents are fixed inside each of the one or two second orifices;

the first inner chimney stent is sutured along an inner wall of the proximal segment, the one or two second inner chimney stents are sutured along an inner wall of the first step, and the one or two second inner chimney stents are sutured along an inner wall of the second step;

one of the plurality of branch arterial stent-grafts is placed inside each of the first inner chimney stent and the second inner chimney stent; and no orifice is formed on a left side wall of the distal segment.

2. The aortic stent-graft according to claim 1, wherein the main aortic stent-graft is in a straight cylindrical shape or a pre-curved shape.

3. The aortic stent-graft according to claim 1, wherein a left segment of the distal segment is connected to the depressed segment, and the left segment of the distal segment gradually expands from left to right.

4. The aortic stent-graft according to claim 1, wherein a right end surface of the second step is an inclined surface, and the inclined surface forms an obtuse angle with an axis of the main aortic stent-graft; and each of the one or two second orifices is an oblique incision formed on the inclined surface.

5. The aortic stent-graft according to claim 1, wherein a second orifice is formed on an upper part of each of the right side wall of the first step and a right side wall of the second step, and the second inner chimney stent is fixed inside the second orifice.

6. The aortic stent-graft according to claim 1, wherein a second orifice is formed on an upper part of the right side wall of the first step, two second orifices are formed on a right side wall of the second step, and the second inner chimney stent is fixed inside each of the second orifice and the two second orifices.

7. The aortic stent-graft according to claim 1, further comprising a plurality of built-in guide wires, wherein one of the plurality of built-in guide wires is placed inside the first inner chimney stent and/or the second inner chimney stent.

* * * * *